United States Patent [19]
White et al.

[11] Patent Number: 5,318,770
[45] Date of Patent: Jun. 7, 1994

[54] TRIFLUOROMETHYL ANALOGS OF X-RAY CONTRAST MEDIA FOR MAGNETIC RESONANCE IMAGING

[75] Inventors: David H. White; Steven R. Woulfe, both of Ballwin; Youlin Lin, Chesterfield; Mills T. Kneller, University City, all of Mo.

[73] Assignee: Mallinckrodt Medical, Inc., St. Louis, Mo.

[21] Appl. No.: 782,153

[22] Filed: Oct. 25, 1991

[51] Int. Cl.$^5$ .................... A61B 5/055; C07C 69/76; C07C 63/04; C07C 233/00
[52] U.S. Cl. .......................... 424/9; 424/5; 436/173; 128/653.4; 514/538; 514/568; 514/604; 514/617; 560/65; 562/493; 564/90; 564/183
[58] Field of Search ............ 424/9, 5; 436/173; 128/653.4, 654; 514/492, 502, 568, 538, 604, 617; 560/65; 562/493; 564/90, 183

[56] References Cited

U.S. PATENT DOCUMENTS

| | | | |
|---|---|---|---|
| 2,247,880 | 7/1941 | Guerbert | 562/480 |
| 3,401,033 | 12/1961 | Jansen et al. | 544/172 |
| 4,547,347 | 10/1985 | Pfeiffer et al. | 424/5 |
| 4,612,185 | 9/1986 | Dean | 424/2 |
| 4,639,364 | 1/1987 | Hoey | 424/9 |

FOREIGN PATENT DOCUMENTS

| | | |
|---|---|---|
| 0165728 | 12/1985 | European Pat. Off. |
| 0122000 | 3/1986 | European Pat. Off. |
| 307863 | 3/1989 | European Pat. Off. |
| 368429 | 5/1990 | European Pat. Off. |
| 03693 | 5/1989 | PCT Int'l Appl. |
| 01759 | 2/1991 | PCT Int'l Appl. |

OTHER PUBLICATIONS

Ghauri, Fyk Methodol. Surv. Biochem. Anal. 20:321–4 (1990).
Ghauri, Fyk J. Pharmaceutical & Chemical Analysis 88-12):939–44 (1990).
B. Gong et al., "Parameter Optimization and Calibration of $^{19}$F Magnetic Resonance Imaging at 1.5 Tesla", Magnetic Resonance Imaging, vol. 9, pp. 101–106 (1991).
R. Mason et al., "Perfluorocarbon Imaging In Vivo: A $^{19}$F MRI Study in Tumor-Bearing Mice", Magnetic Resonance Imaging, vol. 7, pp. 475–485 (1989).
A. Ratner et al., "$^{19}$F Relaxation Rate Enhancement and Frequency Shift with Gd-DTPA", Investigative Radiology, vol. 24, pp. 224–227, (Mar. 1989).
H. Bauer, "$^{19}$F Imaging and Spectroscopy-Efficacy of Contrast Media", SMRM, p. 148, (Aug. 1988).
A. Ratner et al., "Fluorine-19 Relaxation Rate Enhancement with Gadolinium DTPA", SMRM, p. 263 (1986).
N. Iriguchi et al., "In Vivo $^{19}$F Images Obtained within Minutes", SMRM, pp. 1545–1546 (1986).
S. Horner et al., "Evaluation of Myocardial Perfusion by $^{19}$F NMR Imaging", SMRM, pp. 338–339 (1984).

*Primary Examiner*—Gary E. Hollinden
*Attorney, Agent, or Firm*—Brian K. Stierwalt

[57] ABSTRACT

Methods and compositions are disclosed for enhancing $^{19}$F magnetic resonance imaging which utilize trifluorometyl derivatives of iodinated X-ray contrast media. Typical magnetic resonance contrast media within the scope of the present invention include bis(trifluoromethyl)benzene derivatives, tris(trifluoromethyl)benzene derivatives, tetrakis(trifluoromethyl)benzene derivatives, and other related trifluoromethylated benzene derivatives.

9 Claims, No Drawings

TRIFLUOROMETHYL ANALOGS OF X-RAY CONTRAST MEDIA FOR MAGNETIC RESONANCE IMAGING

BACKGROUND OF THE INVENTION

This invention relates to compositions for improving magnetic resonance imaging ("MRI"), magnetic resonance spectroscopy ("MRS"), and magnetic resonance spectroscopy imaging ("MRSI"). More particularly, the present invention relates to low concentration fluorine-19 imaging agents.

The technique of MRI encompasses the detection of certain atomic nuclei (those possessing magnetic dipole moments) utilizing magnetic fields and radio-frequency radiation. It is similar in some respects to X-ray computed tomography ("CT") in providing a cross-sectional display of the body organ anatomy with excellent resolution of soft tissue detail. The technique of MRI is advantageously non-invasive as it avoids the use of ionizing radiation.

The hydrogen atom, having a nucleus consisting of a single unpaired proton, has the strongest magnetic dipole moment of any nucleus. Since hydrogen occurs in both water and lipids, it is abundant in the human body. Therefore, MRI is most commonly used to produce images based upon the distribution density of protons and/or the relaxation times of protons in organs and tissues. Other nuclei having a net magnetic dipole moment also exhibit a nuclear magnetic resonance phenomenon which may be used in MRI, MRS, and MRSI applications. Such nuclei include carbon-13 (six protons and seven neutrons), fluorine-19 (9 protons and 10 neutrons), sodium-23 (11 protons and 12 neutrons), and phosphorus-31 (15 protons and 16 neutrons).

While the phenomenon of MRI was discovered in 1945, it is only relatively recently that it has found application as a means of mapping the internal structure of the body as a result of the original suggestion of Lauterbur (*Nature*, 242, 190-191 (1973)). The fundamental lack of any known hazard associated with the level of the magnetic and radio-frequency fields that are employed renders it possible to make repeated scans on vulnerable individuals. Additionally, any scan plane can readily be selected, including transverse, coronal, and sagittal sections.

In an MRI experiment, the nuclei under study in a sample (e.g. protons, $^{19}F$, etc.) are irradiated with the appropriate radio-frequency (RF) energy in a controlled gradient magnetic field. These nuclei, as they relax, subsequently emit RF energy at a sharp resonance frequency. The resonance frequency of the nuclei depends on the applied magnetic field.

According to known principles, nuclei with appropriate spin when placed in an applied magnetic field (B, expressed generally in units of gauss or Tesla ($10^4$ gauss)) align in the direction of the field. In the case of protons, these nuclei precess at a frequency, F, of 42.6 MHz at a field strength of 1 Tesla. At this frequency, an RF pulse of radiation will excite the nuclei and can be considered to tip the net magnetization out of the field direction, the extent of this rotation being determined by the pulse, duration and energy. After the RF pulse, the nuclei "relax" or return to equilibrium with the magnetic field, emitting radiation at the resonant frequency. The decay of the emitted radiation is characterized by two relaxation times, $T_1$ and $T_2$. $T_1$ is the spin-lattice relaxation time or longitudinal relaxation time, that is, the time taken by the nuclei to return to equilibrium along the direction of the externally applied magnetic field. $T_2$ is the spin-spin relaxation time associated with the dephasing of the initially coherent precession of individual proton spins. These relaxation times have been established for various fluids, organs, and tissues in different species of mammals.

For protons and other suitable nuclei, the relaxation times $T_1$ and $T_2$ are influenced by the environment of the nuclei (e.g., viscosity, temperature, and the like). These two relaxation phenomena are essentially mechanisms whereby the initially imparted radio-frequency energy is dissipated to the surrounding environment. The rate of this energy loss or relaxation can be influenced by certain molecules or other nuclei which are paramagnetic. Chemical compounds incorporating these paramagnetic molecules or nuclei may substantially alter the $T_1$ and $T_2$ values for nearby nuclei having a magnetic dipole moment. The extent of the paramagnetic effect of the given chemical compound is a function of the environment within which it finds itself.

In MRI, scanning planes and sliced thicknesses can be selected. This selection permits high quality transverse, coronal and sagittal images to be obtained directly. The absence of any moving parts in MRI equipment promotes a high reliability. It is believed that MRI has a greater potential than CT for the selective examination of tissue characteristics. The reason for this being that in CT, X-ray attenuation and coefficients alone determine image contrast, whereas at least four separate variables ($T_1$, $T_2$, proton density, and flow) may contribute to the MRI signal. For example, it has been shown (Damadian, *Science*, 171, 1151 (1971)) that the values of the $T_1$ and $T_2$ relaxation in tissues are generally longer by about a factor of two (2) in excised specimens of neoplastic tissue compared with the host tissue.

By reason of its sensitivity to subtle physiochemical differences between organs and/or tissues, it is believed that MRI may be capable of differentiating different tissue types and in detecting diseases which induce physicochemical changes that may not be detected by X-ray or CT which are only sensitive to differences in the electron density of tissue.

In some cases, the concentration of nuclei to be measured is not sufficiently high to produce a detectable MR signal. For instance, since $^{19}F$ is present in the body in very low concentration, a fluorine source must be administered to a subject to obtain a measurable $^{19}F$ MR signal. Signal sensitivity is improved by administering higher concentrations of fluorine or by coupling the fluorine to a suitable "probe" which will concentrate in the body tissues of interest. High fluorine concentration must be balanced against increased tissue toxicity. It is also currently believed that a fluorine agent should preferably contain magnetically equivalent fluorine atoms in order to obtain a clear, strong signal.

From the foregoing, it would be a significant advancement in the art to provide fluorine MRI agents for enhancing images of body organs and tissues which may be administered in relatively low concentrations, yet provide a clear, strong signal.

Such MRI agent are disclosed and claimed herein.

SUMMARY OF THE INVENTION

The present invention provides methods and compositions for improved magnetic resonance imaging and spectroscopy, including fluorine-19 MRI agents. The MRI agents are derived from the class iodinated X-ray contrast media ("XRCM"). Over the years, a number of triiodinated benzene derivatives have been developed and brought to market as XRCM. The XRCM that have been brought successfully to market have had very low toxicity because of the large doses required for X-ray imaging.

Since the doses required for proton magnetic resonance imaging are considerably lower than XRCM doses, magnetic resonance contrast media ("MRCM") which are structurally similar to XRCM should result in a product having a high safety index (the ratio of toxic dose to imaging dose). Even if the MRCM is $^{19}F$ based, the doses should be less than that for XRCM such that the resulting $^{19}F$ MRCM has a high safety index.

The present invention takes advantage of the low toxicity of triiodinated benzyl XRCM by replacing the iodine with trifluoromethyl ("$CF_3$") groups or groups containing $CF_3$. Typical $CF_3$ analogs of XRCM within the scope of the present invention include bis(trifluoromethyl)benzene derivatives, tris(trifluoromethyl)benzene derivatives, tetrakis(trifluoromethyl)benzene derivatives, and other related trifluoromethylated benzene derivatives.

Both iodine and $CF_3$ are similar in size. Therefore, $CF_3$ replacement of iodine does not introduce steric effects that would affect chemical and biological stability. Moreover, the $CF_3$ groups are chemically and biologically inert like iodine. The $CF_3$ substituted MRCM within the scope of the present invention may be prepared such that all the fluorines are substantially chemically equivalent to avoid imaging problems associated with non-equivalent nuclei.

Preparation of $CF_3$ substituted MRCM with 2–4 $CF_3$ groups would have 6–12 fluorines per molecule, thereby improving the efficacy of the molecule and lowering the imaging dose and raising the safety index.

Also disclosed are diagnostic compositions and methods of performing MR diagnostic procedures which involve administering to a warm-blooded animal a diagnostically effective amount of the above-described fluorine substituted MRCM compositions and then exposing the warm-blooded animal to a MR procedure.

DETAILED DESCRIPTION OF THE INVENTION

The present invention provides novel fluorine MRCM. The MRCM of the present invention are trifluoromethyl derivatives of XRCM. For example, a number of triiodo benzene XRCM are modified within the scope of the present invention by replacing iodine with $CF_3$ groups or with $CF_3$ substituted nitroxide radicals. Typical trifluoromethyl XRCM derivatives within the scope of the present invention include (a) bis(trifluoromethyl)benzene derivatives, (b) tris(trifluoromethyl)benzene derivatives, (c) tetrakis(trifluoromethyl)-benzene derivatives, and (d) other related trifluoromethylated benzene derivatives. Generic structures for these trifluoromethyl MRCM compounds follows:

(a) bis(trifluoromethyl)benzene derivatives:

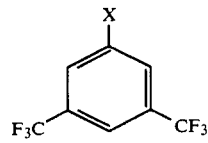

where X may be: $-CONR_1R_2$, $-NR_1COR_2$, $-SO_2NR_1R_2$, $-CO_2H$, and pharmaceutically acceptable salts thereof, and where $R_1$ and $R_2$ may be same or different and are from the group: H, alkyl, and hydroxyalkyl, but usually at least one hydroxyalkyl. The following is an example of a bis(trifluoromethyl)benzene derivative within the scope of the present invention:

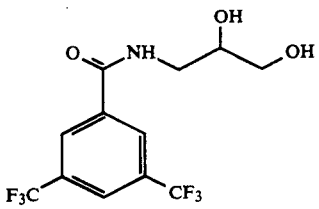

(b) Tris(trifluoromethyl)benzene derivatives:

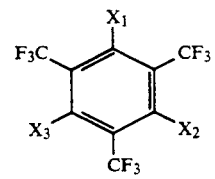

where $X_1$, $X_2$, and $X_3$ may be: $-H$, $-CONR_1R_2$, $-NR_1COR_2$, $-SO_2NR_1R_2$, $-CO_2H$, and pharmaceutically acceptable salts thereof, and where $R_1$ and $R_2$ may be same or different and are from the group: H, alkyl, and hydroxyalkyl, but usually at least one is hydroxyalkyl. The following are examples of tris(trifluoromethyl)benzene derivatives within the scope of the present invention:

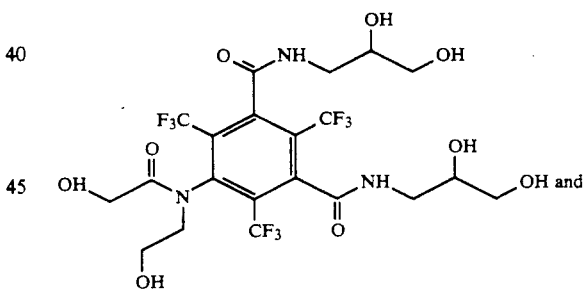

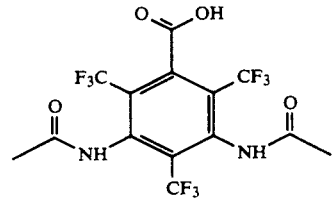

(c) Tetrakis(trifluoromethyl)benzene derivatives:

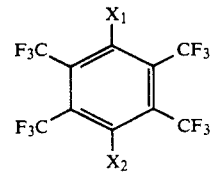

where $X_1$ and $X_2$ may be: $-CONR_1R_2$, $-NR_1COR_2$, $-SO_2NR_1R_2$, $-CO_2H$, and pharmaceutically acceptable salts thereof, and where $R_1$ and $R_2$ may be same or different and are from the group: H, alkyl, and hydroxyalkyl, but usually at least one is hydroxyalkyl. The following is an example of a tetrakis(trifluoromethyl)benzene derivative within the scope of the present invention:

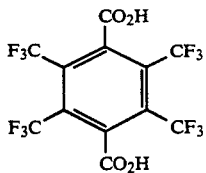

(d) Other related trifluoromethylbenzene derivatives:

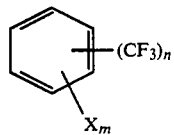

where x may be: $-CONR_1R_2$, $-NR_1COR_2$, $-SO_2NR_1R_2$, $-CO_2H$, and pharmaceutically acceptable salts thereof, and where $R_1$ and $R_2$ may be same or different and are from the group: H, alkyl, and hydroxyalkyl, but usually at least one is hydroxyalkyl, and where $n=1-5$ and $m=6-n$.

The $CF_3$ substituted MRCM within the scope of the present invention are preferably prepared such that all the fluorines are substantially chemically equivalent to avoid imaging problems associated with non-equivalent nuclei. In addition, the $CF_3$ substituted MRCM may be prepared with a large number of fluorine atoms per molecule, thereby improving the efficacy of the molecule and lowering the imaging dose.

The $^{19}F$ MRCM compounds of this invention are preferably formulated into diagnostic compositions for enteral or parenteral administration. The MRCM formulations may contain conventional pharmaceutical carriers and excipients appropriate for the type of administration contemplated.

For example, parenteral formulations for $^{19}F$ imaging advantageously contain a sterile aqueous solution or suspension of a trifluoromethyl MRCM according to this invention. Various techniques for preparing suitable pharmaceutical solutions and suspensions are known in the art. Such solutions also may contain pharmaceutically acceptable buffers, stabilizers, antioxidants, and electrolytes, such as sodium chloride. Parenteral compositions may be injected directly or mixed with a large volume parenteral composition for systemic administration.

Formulations for enteral administration may vary widely, as is well-known in the art. In general, such formulations include a diagnostically effective amount of a $^{19}F$ MRCM in an aqueous solution or suspension. Such enteral compositions may optionally include buffers, surfactants, adjuvants, thixotropic agents, and the like. Compositions for oral administration may also contain flavoring agents and other ingredients for enhancing their organoleptic qualities.

The diagnostic compositions within the scope of the present invention are administered in doses effective to achieve the desired enhancement of the NMR image.

Such doses may vary widely, depending upon the degree of fluorination, the organs or tissues which are the subject of the imaging procedure, the NMR imaging equipment being used, etc. Typical doses of the diagnostic compositions are in the range from about 0.005 to about 20 mmol/kg body weight, and preferably in the range from about 0.05 to about 5 mmol/kg body weight.

It has been found that the addition of paramagnetic species to the diagnostic compositions greatly improves the relaxation properties of $^{19}F$ and the resulting $^{19}F$ image. The paramagnetic species may be administered in doses from about 1 $\mu$mol/kg body weight to about 2 mmol/kg body weight, and preferably in doses from about 50 $\mu$mol/kg to about 0.5 mmol/kg body weight. Typical paramagnetic species include well known complexes of paramagnetic metal ions.

In general, complexes of paramagnetic metal ions of elements with an atomic number of 21 to 29, 42 to 44, and 58 to 70 may improve the relaxivity of $^{19}F$. Suitable such ions include chromium(III), manganese(II), manganese(III), iron(II), iron(III), cobalt(II), nickel(II), copper(II), praseodymium(III), neodymium(III), samarium(III) and ytterbium(III). Because of their very strong magnetic moments, gadolinium(III), terbium(III), dysprosium(III), holmium(III) and erbium(III) are preferred.

The diagnostic compositions of this invention are used in a conventional manner in magnetic resonance procedures. Compositions may be administered in a sufficient amount to provide adequate visualization, to a warm-blooded animal either systemically or locally to an organ or tissues to be imaged, and the animal then subjected to the MRI procedure. The compositions enhance the magnetic resonance images obtained by these procedures.

The following examples are offered to further illustrate the present invention. These examples are intended to be purely exemplary and should not be viewed as a limitation on any claimed embodiment.

EXAMPLE 1

Synthesis of N-(2,3-dihydroxypropyl)-3,5-bis(trifluoromethyl)-benzenecarboxamide N-(2,3-dihydroxypropyl)-3,5-bis(trifluoromethyl)-benzenecarboxamide, a bis(trifluoromethyl)benzene derivative, is prepared by dissolving 4.2 g (50 mmol) sodium bicarbonate and 4.6 g (50 mmol) 3-amino-1,2-propanediol in 50 mL of water. A solution of 3,5-bis(trifluoromethyl) benzoyl chloride (13.8 g, 50 mmol) in 50 mL of toluene is added. The heterogeneous mixture is stirred for 18 hours at room temperature. The mixture is poured into a separatory funnel. The aqueous layer is separated, washed with ether and evaporated. The residue is purified by $C_{18}$ chromatography to give the amide, N-(2,3-dihydroxypropyl)-3,5-bis(trifluoromethyl)-benzenecarboxamide. The chemical reaction is shown below:

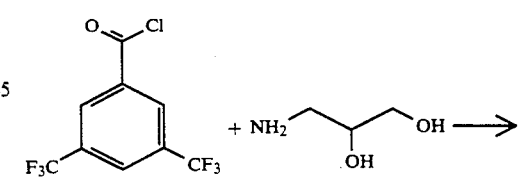

-continued

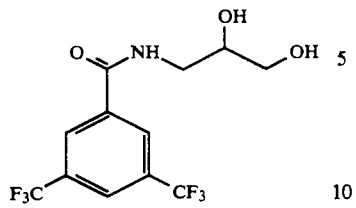

EXAMPLE 2

Synthesis of N,N'-bis(2,3-dihydroxypropyl)-5-[(hydroxyacetyl)-(2-hydroxyethyl)-amino]-2,4,6-tris(trifluoromethyl)-1,3-benzenedicarboxamide N,N'-bis(2,3-dihydroxypropyl)-5-[(hydroxyacetyl)-(2-hydroxyethyl)-amino]-2,4,6-tris(trifluoromethyl)-1,3-benzenedicarboxamide, a tris(trifluoromethyl)benzene derivative, is prepared as follows: a mixture of N,N'-bis(2,3-dihydroxypropyl)-5[(hydroxyacetyl)-(2-hydroxyethyl)-amino]-2,4,6-triiodo-1,3-benzenedicarboxamide (20 g, 25 mmol), sodium trifluoroacetate (61.2 g, 450 mmol), and copper(I) iodide (42.8 g, 225 mmol) in 500 mL of N,N-dimethylacetamide is refluxed under argon for six hours. The solvent is evaporated. The product is isolated from the crude residue by $C_{18}$ chromatography. The chemical reaction is shown below:

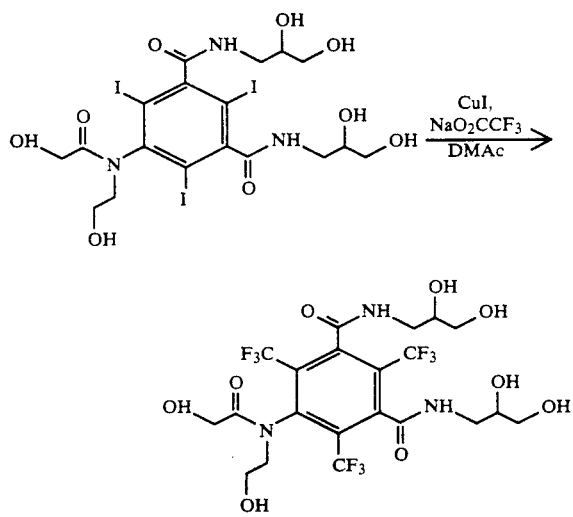

EXAMPLE 3

Synthesis of 3,5-Bis(acetylamino)-2,4,6-tris(trifluoromethyl) benzenecarboxylic acid, meglumine salt 3,5-Bis(acetylamino)-2,4,6-tris(trifluoromethyl) benzenecarboxylic acid, a tris(trifluoromethyl)benzene derivative, is prepared according to the procedure of Example 2, except that 3,5-Bis(acetylamino)-2,4,6-triiodo benzenecarboxylic acid is used instead of N,N'-bis(2,3-dihydroxypropyl)-5[(hydroxyacetyl)-(2-hydroxyethyl)-amino]-2,4,6-triiodo-1,3-benzenedicarboxamide. The chemical reaction is shown below:

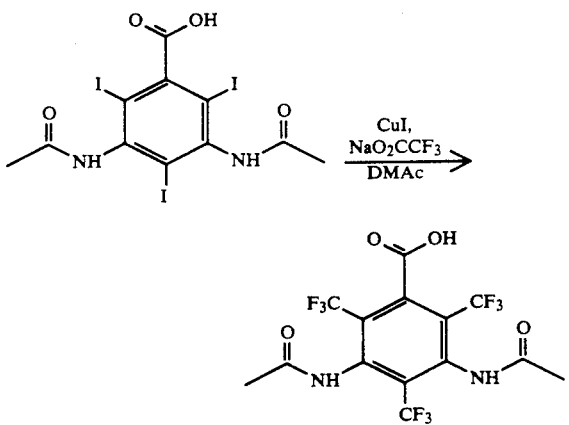

EXAMPLE 4

Synthesis of 2,3,5,6-tetrakis(trifluoromethyl)-1,4-benzenedicarboxylic acid, dimeglumine salt 2,3,5,6-tetrakis(trifluoromethyl)-1,4-benzenedicarboxylic acid is prepared by charging a one liter stainless-steel autoclave with 1,2,4,5-benzenetetracarboxylic acid (51 g, 200 mmol) then cooled in liquid nitrogen. Hydrogen fluoride (100 g, 5.0 mol) and sulfur tetrafluoride (173 g, 1.6 mol) are added. The autoclave is sealed and heated at 150° C. for six hours. The gases are vented and the contents are poured onto ice. The mixture is transferred to a separatory funnel and extracted into ether. The ether layers are washed with dilute sodium hydroxide, dried over magnesium sulfate, filtered and evaporated to leave crude product. Recrystallization is used to give pure 1,2,4,5-tetrakis(trifluoromethyl)benzene. The chemical reaction is shown below:

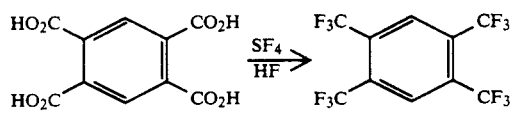

A solution of n-butyl lithium (6.4 g, 100 mmol) in hexanes is added at room temperature to a solution of 1,2,4,5-tetrakis(trifluoromethyl)benzene (16.9 g, 50 mmol) 200 mL of anhydrous ether under argon. After one hour the reaction mixture is poured onto dry ice. The mixture is taken up into water, washed with ether and acidified to pH 2, The product is extracted into ether, washed with water and brine, dried over magnesium sulfate, filtered and evaporated, The crude product is recrystallized. The dimeglumine salt is prepared by adding two equivalents of N-methyl-D-Glucamine in appropriate solvent.

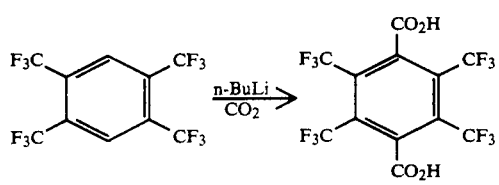

From the foregoing, it will be appreciated that the present invention provides fluorine MRI agents for enhancing images of body organs and tissues which may be administered in relatively low concentrations, yet provide a clear, strong signal.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for obtaining fluorine-19 magnetic resonance images of body organs and tissues which comprises:
   (a) administering to a mammal, a diagnostically effective amount of a trifluoromethyl benzene derivative in a pharmaceutically acceptable carrier, said trifluoromethyl benzene derivative having a general formula:

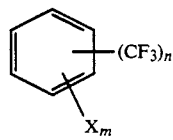

where X is —$CONR_1R_2$, —$NR_1COR_2$, —$SO_2NR_1R_2$, —$CO_2H$, or pharmaceutically acceptable salts thereof, and where $R_1$ and $R_2$ may be same or different and are selected from the group consisting of H, alkyl, and hydroxyalkyl, and where n is in the range from 1 to 5 and m=6—n; and
   (b) imaging the organs and tissues.

2. A method for obtaining fluorine-19 magnetic resonance images of body organs and tissues which comprises:
   (a) administering to a mammal, a diagnostically effective amount of a trifluoromethyl benzene derivative in a pharmaceutically acceptable carrier, said trifluoromethyl benzene derivative having a general formula:

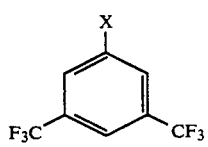

where X is —$CONR_1R_2$, —$NR_1COR_2$, —$SO_2NR_1R_2$, —$CO_2H$, or pharmaceutically acceptable salts thereof, and where $R_1$ and $R_2$ may be same or different and are selected from the group consisting of H, alkyl, and hydroxyalkyl; and
   (b) imaging the organs and tissues.

3. A method for obtaining fluorine-19 magnetic resonance images as defined in claim 2, wherein the trifluoromethylbenzene derivative includes:

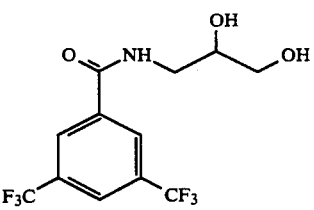

4. A method of obtaining fluorine-19 magnetic resonance images of body organs and tissues which comprises:
   (a) administering to a mammal, a diagnostically effective amount of a trifluoromethyl benzene derivative in a pharmaceutically acceptable carrier, said trifluoromethyl benzene derivative having a general formula:

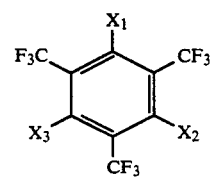

where $X_1$, $X_2$, and $X_3$ are —H, —$CONR_1R_2$, —$NR_1COR_2$, —$SO_2NR_1R_2$, —$CO_2H$, or pharmaceutically acceptable salts thereof, and where $R_1$ and $R_2$ may be same or different and are selected from the group consisting of H, alkyl, and hydroxyalkyl; and
   (b) imaging the organs and tissues.

5. A method for obtaining fluorine-19 magnetic resonance images as defined in claim 4, wherein the trifluoromethylbenzene derivative includes:

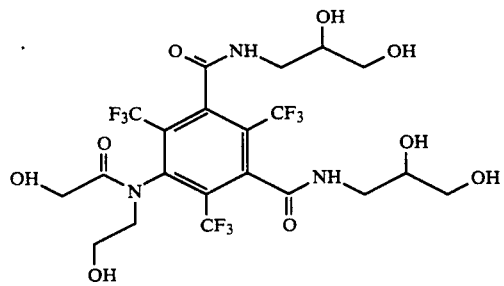

6. A method for obtaining fluorine-19 magnetic resonance images as defined in claim 4, wherein the trifluoromethylbenzene derivative includes:

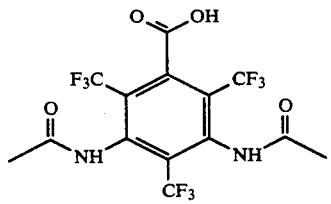

7. A method for obtaining fluorine-19 magnetic resonance images of body organs and tissues which comprises:
   (a) administering to a mammal, a diagnostically effective amount of a trifluoromethyl benzene derivative in a pharmaceutically acceptable carrier, said trifluoromethyl benzene derivative having a general formula:

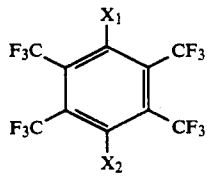

where $X_1$ and $X_2$ are —H, —CONR$_1$R$_2$, —NR$_1$COR$_2$, —SO$_2$NR$_1$R$_2$, —CO$_2$H, or pharmaceutically acceptable salts thereof, and where R$_1$ and R$_2$ may be same or different and are selected from the group consisting of H, alkyl, and hydroxyalkyl; and (b) imaging the organs and tissues.

8. A diagnostic composition suitable for enteral or parenteral administration to a warm-blooded animal comprising:

a diagnostically effective amount of a trifluoromethylbenzene derivative having a general formula:

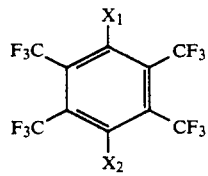

where $X_1$, $X_2$, and $X_3$ are —H, —CONR$_1$R$_2$, —NR$_1$COR$_2$, —SO$_2$NR$_1$R$_2$, —CO$_2$H, or pharmaceutically acceptable salts thereof, and where R$_1$ and R$_2$ may be same or different and are selected from the group consisting of H, alkyl, and hydroxyalkyl; and a pharmaceutically acceptable carrier.

9. A diagnostic composition suitable for enteral or parenteral administration to a warm-blooded animal comprising:

a diagnostically effective amount of a trifluoromethylbenzene derivative having a general formula:

where $X_1$ and $X_2$ are —H, —CONR$_1$R$_2$, —NR$_1$COR$_2$, —SO$_2$NR$_1$, R$_2$, —CO$_2$H, or pharmaceutically acceptable salts thereof, and where R$_1$ and R$_2$ may be same or different and are selected from the group consisting of H, alkyl, and hydroxyalkyl; and a pharmaceutically acceptable carrier.

* * * * *